United States Patent [19]
Schottle et al.

[11] Patent Number: 5,432,259
[45] Date of Patent: Jul. 11, 1995

[54] PROCESS FOR THE PREPARATION OF FLUORINATED MONOMERS

[75] Inventors: Thomas Schottle, Burghausen; Klaus Hintzer, Kastl; Hans J. Staudt, Haiming; Herbert Weber, Burgkirchen, all of Germany

[73] Assignee: Hoechst Aktiengesellschaft, Frankfurt am Main, Germany

[21] Appl. No.: 317,883

[22] Filed: Oct. 4, 1994

[30] Foreign Application Priority Data

Oct. 6, 1993 [DE] Germany .................... 43 34 015.6

[51] Int. Cl.[6] .................... C07C 21/18; C07C 17/33
[52] U.S. Cl. .................... 528/481; 570/136; 570/152; 570/153
[58] Field of Search ................ 528/481; 570/152, 136, 570/153

[56] References Cited

U.S. PATENT DOCUMENTS 3,832,411 8/1974 Arkles et al. .................... 570/152
4,076,760 2/1978 Hartwimmer .................... 570/152

OTHER PUBLICATIONS

Dissertation by Jurgen Merkel, U. of Hamburg, Faculty of Chemistry, 1982.

*Primary Examiner*—Morton Foelak

[57] ABSTRACT

The pyrolysis of fluorine polymers leads to a high yield of pure fluorinated monomers if the finely divided polymer is introduced, with steam, into a fluidized bed reactor which contains an inert, granular material as the fluidized material, the steam functioning as the fluidizing gas.

9 Claims, 1 Drawing Sheet

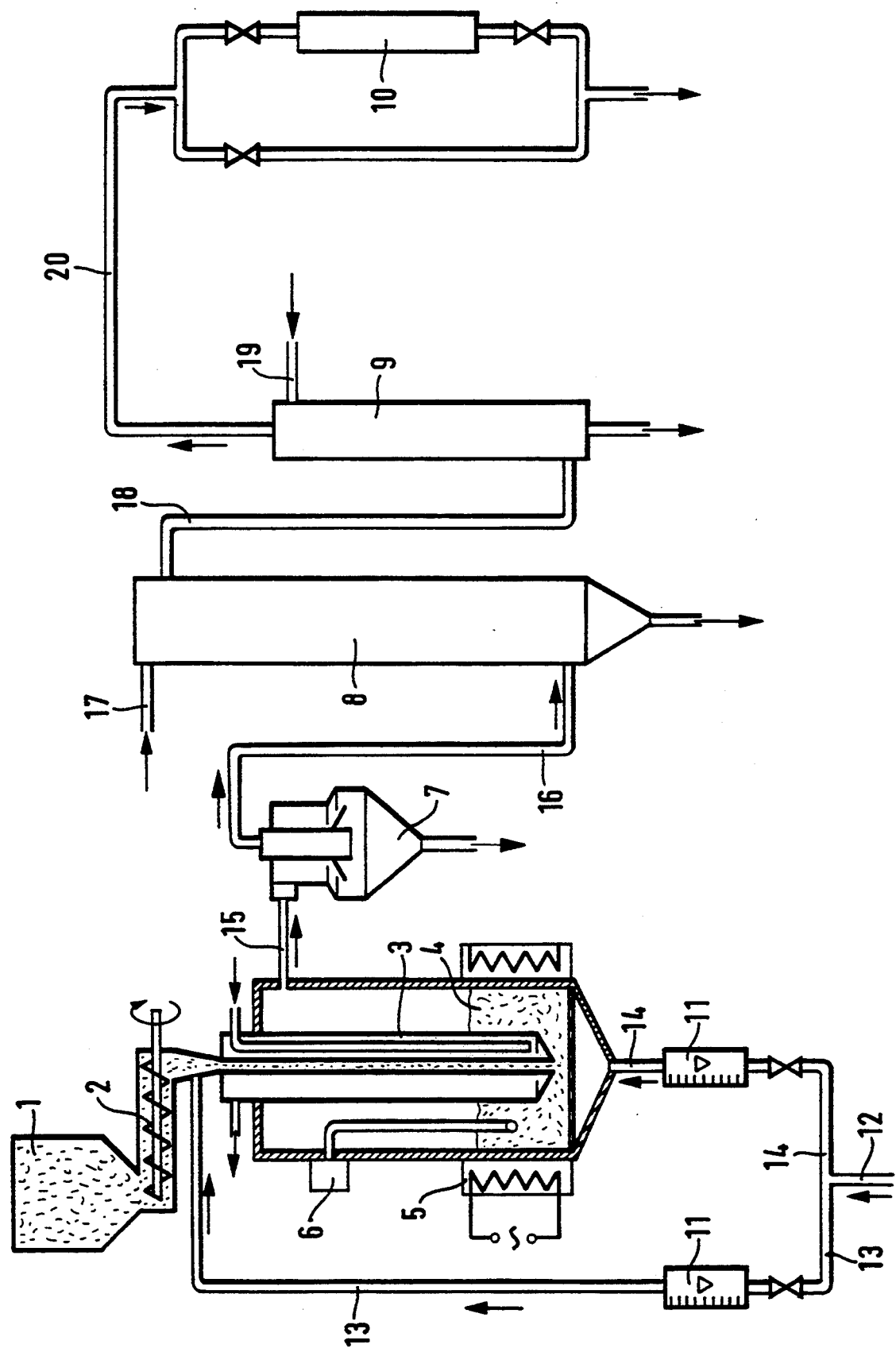

PROCESS FOR THE PREPARATION OF FLUORINATED MONOMERS

DESCRIPTION

The recovery of fluorinated monomers by pyrolysis of fluoro polymers is known. Thus, for example, U.S. Pat. No. 3,832,411 relates to a process for the preparation of tetrafluoroethylene by pyrolysis of polytetrafluoroethylene by carrying out the pyrolysis by heating with steam at a temperature of between about 405° and 760° C. and without using reduced pressure, the molar ratio of steam to the pyrolysis products being at least 1:1. In this process, the polytetrafluoroethylene is applied to a porous surface, for example to a wire sieve, and is also covered or enclosed with a sieve material. This is said to prevent some of the solid raw material from being blown upwards by the steam and the gaseous decomposition products. The molten polytetrafluoroethylene flows through the porous substrate and thereby forms stalactites, while the hot steam present must decompose the polymer before drops of the melt can reach the bottom of the container. Implementation and control of this process is therefore very expensive and in practice is only possible batchwise.

It has now been found that this process becomes readily controllable if the fluoro polymer to be pyrolyzed is introduced continuously into a heated fluidized bed reactor which contains inert, granular material as the fluidized material. Steam is used as the fluidizing gas.

The pyrolysis of polytetrafluoroethylene in a fluidized bed is known from the dissertation by Jürgen Merkel, University of Hamburg, Faculty of Chemistry, 1982. In this process, the polymer is introduced into a fluidized sand bed at a temperature of 720° to 790° C., specifically at 760° and 790° C. In contrast to the process according to the invention, a portion of the gaseous cleavage products is recycled to the reactor as fluidizing medium. The yield of tetrafluoroethylene here is less than 5% by weight, that of hexafluoropropene is 22% by weight and that of perfluorocyclobutane (which, as the dimer of tetrafluoroethylene, is counted here among the desired "monomers") and perfluorobut-1-ene together is 32 to 37% by weight. At lower temperatures (for example 650° C.), about 38% by weight of waxy products are formed, which lead to caking on the walls, sticking together and blockages. About 2% by weight of liquid products are also formed. This process has therefore acquired no importance.

In contrast to this known process, the desired monomers are obtained in high yields and practically without troublesome higher molecular weight pyrolysis products in the fluidized bed method according to the invention. Preferred embodiments of the invention are explained in more detail below.

Suitable starting materials are fluorinated homo- and copolymers in the form of pure polymers, mixtures of various polymers and also mixtures of polymers with fillers, such as carbon, glass or metals. Pastes and dispersions of such polymeric substances are also suitable. The homopolymer of tetrafluoroethylene, also together with fillers, such as carbon in the form of graphite or charcoal, glass or metals, such as bronze, is preferred. In general, all fillers which do not form troublesome byproducts during the pyrolysis or do not impair the pyrolysis itself are suitable.

The fluidized bed is maintained by introducing steam as the fluidizing medium. The use of inert gases as the fluidizing medium is in general not advantageous, since these make isolation of the monomers formed more difficult.

Mineral substances, such as sand, glass, ceramic, metal oxides, such as aluminum oxide, and similar inert substances, are employed as the fluidized material.

The pyrolysis temperature is in general between 500° and 900° C. The heat required for the pyrolysis can be supplied either via the heated steam or by additional direct or indirect heating, for example of the reactor wall. The preferred pyrolysis temperature is in the range from 600° to 750° C., in particular in the range from 625° to 675° C.

After the pyrolysis, the mixture of steam and pyrolysis products is freed from entrained particles of solids in a cyclone and cooled rapidly by spraying in water, the steam condensing out. The pyrolysis products are then dried, for example with concentrated sulfuric acid, and subjected to fractional distillation.

The process according to the invention leads to a high yield of usable fluorinated monomers. In the case of polytetrafluoroethylene, tetrafluoroethylene, hexafluoropropene and perfluorocyclobutane are obtained in a virtually quantitative yield. Liquid or solid pyrolysis byproducts are formed only to an extremely low extent.

BRIEF DESCRIPTION OF THE DRAWING

The sole FIGURE of the accompanying drawing schematically illustrates an apparatus suitable for carrying out the process of this invention.

The invention is illustrated in more detail in the following examples.

EXAMPLES

A diagram of the apparatus employed in the following examples is shown in the figure. In this, (1) is a storage hopper, (2) is a metering screw, (3) is a coolable downpipe, (4) is the fluidized bed, (5) is (electrical) heating, (6) is a temperature probe (thermocouple) couple), (7) is a cyclone, (8) is a cooler (quench cooler), (9) is a washer, (10) is a container with a sampling device and (11) is a gas meter (rotameter). (12) is the line from the steam generator, the steam being passed via lines (13) and (14) into the fluidized bed. The pyrolysis gases pass via line (15) to the cyclone (7), and from there via line (16) to the cooler (8), which is charged with water via line (17). From the cooler (8), the pyrolysis gases then pass via line (18) to the washer (9), which is charged with sulfuric acid via line (19). The washed pyrolysis gases then pass via line (20) to the container with the sampling device (10).

EXPERIMENTAL PROCEDURE

The storage hopper (1) contains ground polytetrafluoroethylene (PTFE) having an average particle diameter of about 0.5 mm. This is passed continuously, with the aid of the metering screw (2), through the cooled downpipe (3) with steam from line (13) into the heated sand fluidized bed (4). This fluidized bed comprises 140 g of sea sand having a particle size of 0.3 to 0.4 mm. The pyrolysis temperature (temperature of the sand fluidized bed) is stated below in the examples. The fluidized bed is 5 cm high, at a diameter of 7 cm. Additional steam (40% of the total amount) comes through the inflow base, which forms the lower limit of the fluidized bed (4), from the bottom through line (14). The steam temperature is 500° C. and the rate of introduction through line (12) is 5 g/min. Distribution of the amount of steam, that is to say 60% by volume via line (13) and 40% by volume via line (14), is controlled via valves and the rotameters (11). The pressure is 1 bar absolute.

The gaseous pyrolysis products leave the fluidized bed (4) with the steam via line (15) and are freed from entrained particles of solids in the cyclone (7). The gases then pass via line (16) into the quench cooler (8), in which the reaction gases are cooled by spraying in water, fed in via line (17), the steam condensing out. The pyrolysis gases then pass via line (18) to the washer (9), which is charged with sulfuric acid via line (19). The gas mixture, dried by the sulfuric acid, then passes via line (20) to the container (10) with sampling device.

Table 1 shows the variable experimental parameters and Table 2 shows the experimental results.

TABLE 1

|  | Example 1 | Example 2 |
|---|---|---|
| Temperature (°C.) | 650 | 700 |
| PTFE introduction rate (g/min) | 2 | 5 |

TABLE 2

| Composition of the pyrolysis gases in % by weight (determined by gas chromatography, with a correction factor) | | |
|---|---|---|
|  | Example 1 | Example 2 |
| Carbon monoxide | 0.4 | 0.8 |
| Trifluoromethane | 0.05 | 0.1 |
| Trifluoroethylene | 0.05 | 0.1 |
| Tetrafluoroethylene | 85.0 | 82.5 |
| Hexafluoropropene | 6.0 | 8.5 |
| Octafluorocyclobutane | 8.0 | 7.5 |
| Others | 0.5 | 0.5 |

We claim:

1. A process for the preparation of fluorinated monomers by pyrolysis of fluorinated polymers in the presence of steam, which comprises carrying out the pyrolysis in a fluidized bed reactor which contains inert, granular material as the fluidized material, and feeding in steam as the fluidizing gas.

2. The process as claimed in claim 1, wherein a said fluorinated polymer is a polymer of essentially tetrafluoroethylene.

3. The process as claimed in claim 1, wherein the pyrolysis is carried out at a temperature of about 500° to 900° C.

4. The process as claimed in claim 2, wherein the pyrolysis is carried out at a temperature of about 500° to 900° C.

5. A process for recovery of a fluorinated monomer from a fluorinated polymer, comprising:

maintaining a fluidized bed by introducing to a pyrolysis zone essentially inert gas-free steam, as essentially the fluidizing medium, and fluidizing therewith an inert, granular material as the fluidized material, feeding a particulate fluorinated polymer to said fluidized bed and pyrolyzing said fluorinated polymer in said fluidized bed, thereby producing gaseous pyrolysis products, and recovering a fluorinated monomer from said gaseous pyrolysis products.

6. The process as claimed in claim 5, wherein said pyrolyzing is carried out at 500° to 900° C.

7. The process as claimed in claim 5, wherein a said fluorinated monomer recovered in accordance with said process is tetrafluoroethylene.

8. The process as claimed in claim 7, wherein a said fluorinated monomer recovered in accordance with said process is hexafluoropropene or octafluorocyclobutane or a mixture thereof.

9. The process as claimed in claim 5, wherein said gaseous pyrolysis products are conveyed from said fluidized bed to a separation zone for separating solids from gases.

* * * * *